US010809171B2

(12) United States Patent
Gasik (10) Patent No.: US 10,809,171 B2
(45) Date of Patent: Oct. 20, 2020

(54) METHOD FOR MEASUREMENT AND MODEL-FREE EVALUATION OF INJECTABLE BIOMATERIALS PROPERTIES

(71) Applicant: Seqvera Ltd. Oy, Helsinki (FI)

(72) Inventor: Michael Gasik, Helsinki (FI)

(73) Assignee: Seqvera Ltd. Oy, Helsinki (FI)

( * ) Notice: Subject to any disclaimer, the term of this patent is extended or adjusted under 35 U.S.C. 154(b) by 329 days.

(21) Appl. No.: 16/040,672

(22) Filed: Jul. 20, 2018

(65) Prior Publication Data

US 2019/0041310 A1    Feb. 7, 2019

Related U.S. Application Data

(60) Provisional application No. 62/541,252, filed on Aug. 4, 2017.

(51) Int. Cl.
| | |
|---|---|
| *G01N 11/00* | (2006.01) |
| *G01N 11/04* | (2006.01) |
| *G01N 33/15* | (2006.01) |
| *A01N 25/04* | (2006.01) |
| *G01N 11/08* | (2006.01) |

(52) U.S. Cl.
CPC ............ *G01N 11/00* (2013.01); *A01N 25/04* (2013.01); *G01N 11/04* (2013.01); *G01N 33/15* (2013.01); *G01N 11/08* (2013.01)

(58) Field of Classification Search
CPC ........ G01N 11/00; G01N 11/04; G01N 11/08; G01N 33/15; G01N 3/08–18; G01N 3/32–38; A01N 25/04; A61L 27/52; A61B 5/6848; A61B 5/6847
See application file for complete search history.

(56) References Cited

U.S. PATENT DOCUMENTS

| | | | | |
|---|---|---|---|---|
| 5,269,190 | A | * | 12/1993 | Kramer ................. G01N 11/00 73/822 |
| 5,808,203 | A | * | 9/1998 | Nolan, Jr. ......... A61M 5/14546 604/67 |
| 2011/0196259 | A1 | * | 8/2011 | Gianchandani .... A61B 10/0233 600/567 |

(Continued)

FOREIGN PATENT DOCUMENTS

DE          4000873 C1    7/1991

OTHER PUBLICATIONS

Aguado B.A., Mulyasasmita W., Su J., Lampe K.J., Heilshorn S.C. Improving viability of stem cells during syringe needle flow through the design of hydrogel cell carriers. Tissue Eng. A18 (2012), 806-815.

(Continued)

*Primary Examiner* — Nathaniel J Kolb
(74) *Attorney, Agent, or Firm* — Berggren LLP (57) ABSTRACT

The invention discloses a method for testing of injectable biomaterials and their performance in the treated materials, to obtain functional properties of the biomaterials and of the specimen injected with that biomaterial. The purpose of the method is to measure these properties during injection of a biomaterial into a target object, then measure the properties of a target object specimen after the injection, and then combine these results using material model-free data processing with possible prediction.

12 Claims, 8 Drawing Sheets

(56) References Cited

U.S. PATENT DOCUMENTS

2014/0038175 A1* 2/2014 Gasik ............... C12Q 1/70
435/5

OTHER PUBLICATIONS

Silva-Correia J., Gloria A., Oliveira M.B., Mano J.F., Oliveira J.M., Ambrosio L., Reis, R.L. Rheological and mechanical properties of acellular and cell-laden methacrylated gellan gum hydrogels. J. Biomed. Mater. Res. A 101 (2013), 3438-3446.

Bencherif S.A., Sands R.W., Bhatta D., Arany P., Verbeke C.S., Edwards D.A., Mooney D.J. Injectable preformed scaffolds with shape-memory properties. PNAS 109 (2012), 19590-19595.

Sánchez-Carpintero I., Candelas D., Ruiz-Rodriguez R. Dermal fillers: types, indications, and complications. Actas Dermosifiliogr. 101 (2010), 381-393.

Sadick N.S., Karcher C., Palmisano L. Cosmetic dermatology of the aging face. Clinics in Dermatol. 27 (2009), S3-S12.

Lujan T.J., Wirtz K.M., Bahney C.S., Madey S.M., Johnstone B., Bottlang M. A novel bioreactor for the dynamic stimulation and mechanical evaluation of multiple tissue-engineered constructs, Tissue Eng. C 17 (2011), 367-374.

Xiao H. Invariant characteristic representations for classical and micropolar anisotropic elasticity tensors. J. Elasticity 40 (1995), 239-265.

Maslov V. The characteristics of pseudo-differential operators and difference schemes. Actes Congrès intern. Math. 2 (1970), 755-769.

Hanyga A., Seredynska M. Power-law attenuation in acoustic and isotropic anelastic media. Geophys. J. Inter. 155 (2003), 830-838.

Gunawardena J. An introduction to idempotency. HP Laboratories Bristol, Publication HPL-BRIMS-96-24 (1996), 50 p.

Gerisch A., Chaplain M.A.J. Robust numerical methods for taxis-diffusion-reaction systems: applications to biomedical problems. Mathem. Computer Model. 43 (2006), 49-75.

Gorenflo R., Luchko Y., Mainardi, F. Analytical properties and applications of the Wright function. Frac. Calc. Appl. Anal. 2 (1999), 383-414.

Norris A. Eulerian conjugate stress and strain. J. Mech. Mater. Stuct. 3 (2008), 243-260.

Draft Guidance for Industry and FDA staff, Silver Spring, MD, USA, Apr. 2013, 13 p.

* cited by examiner

METHOD FOR MEASUREMENT AND MODEL-FREE EVALUATION OF INJECTABLE BIOMATERIALS PROPERTIES

PRIORITY

This application is nonprovisional application of U.S. Provisional Patent application No. 62/541,252 filed 4 Aug. 2017, the contents of which are incorporated herein by reference.

FIELD OF THE INVENTION

The present invention relates to a new method of testing injectable materials, especially biomaterials, allowing measurement, model-free evaluation and possible prediction of plurality of those material properties during and after injection to describe the behavior or performance of that biomaterial at proper conditions.

BACKGROUND OF THE INVENTION

Injectable biomaterials and fluids are of a daily use in medical practice, healthcare and cosmetology. Injection of any material into body tissues causes local perturbation of the tissue due to pressure peaks, influencing adjacent nerves and causing pain feeling. Many applications like injection of a contrast into spine channel, of a corrective substance into intervertebral disk, of β-cells-laden hydrogel into pancreas, or of visco-supplementation into an articulate joint, etc., might have a catastrophic effect causing damage to the organ or somatic system due to improper injection rate. Therefore, knowledge of the viscous properties of the fluids for injectable applications is very important.

The injection process can be performed manually (using hand-driven pressure) or automatically (with sophisticated syringe systems which monitor injection rate or pressure and adjusting the force accordingly to keep the rate constant). The latter however are much less in use, complex, expensive and furthermore are designed for specific product only. For instance, when the fluid in non-Newtonian (its viscosity is stress- or rate-dependent), automatic syringe system cannot know the local shear rate and the instant viscosity, which lead to variable supply of the injected material while the system considers it to be injected evenly.

Most of the current injection devices are designed simply to generate some fluid pressure inside, as this is a fluid pressure gradient between the fluid in the syringe and in the tissue which drives the flow. The pressure in the syringe is measured either indirectly (via measuring motor current in the mechanized drive unit used to apply force to the syringe plunger) or using an embedded load sensor (within the mechanized drive unit). None of these methods however is really practical—even in the case when inaccuracies arising from variation in frictional resistance within the syringe, in the syringe and needle diameter and depth of insertion, in the plunger speed, in the degree of lubrication, in the contact surface between the plunger cover and the syringe wall, in the apparent discontinuities in the plunger movement, etc., etc. are eliminated, this does not give a useful information how much fluid was actually injected at that depth in the tissue and at which rate this has happened.

The injection systems (syringes) are routinely tested on the injection force. However, many such tests, for example by the standard ISO 11040, were criticized by US FDA lacking essential specifications and describing only a testing method of the injection as a stand-alone product [1]. Indeed, pressure measurements using a syringe without a needle and with water as a fluid (ISO 7886, Indian standard IS 10258) do not produce data suitable for another system (especially non-Newtonian) where fluid or hydrogel is being injected into a real tissue with a specific needle size.

In many publications and patents, properties of the injectable fluid are assumed to be known, constant, or being just ignored, focusing explicitly on measurement of the fluid pressure inside the injection device. For example, German patent DE4000873C1 discloses the device of controlling (validating) of pressure inside the infusion apparatus using electronic measuring system connected with the feedback-controlled infusion pump. This invention does not take into account changes in material viscosity, variations in fluid properties, neither effect of the infusion rate or syringe plunger loading patterns.

In another example, U.S. Pat. No. 5,808,203 discloses fluid pressure measuring devices and method of pressure sensing, utilizing a dedicated pressure sensor, which is embedded or connected to the syringe, where the sensor at least partially is connected to the contact surface of the fluid medium. This method also capable only of pressure sensing and is not able to control any other parameters.

Especially in the case of biological fluids (which are known to be non-Newtonian), there is no possibility to know exact stresses and shear rates acting in the syringe space, in the needle and in the target tissue. For example, in publication [2] a simulation of the hydrogel flow from a syringe through a needle (yet into open air) was performed using modeling with computational fluid dynamics, where the stem cells-laden hydrogel behavior was compared with phosphate-buffered saline aqueous solutions. Despite that rheological properties of these materials were measured in advance, revealing links between shear rate and viscosity, it did not help to catch the proper variation of injectability of these fluids. These reported computer simulations results [2] have also shown a huge variation of the shear stress in the syringe and needle spaces, with very high gradients, leading to variations of the shear strain and respectively fluid flow.

In another publication [3] similar study was made with gellan gum hydrogels, the injectability of which was tested with a syringe fixed on a mechanical testing machine and subjected to a force ensuring constant plunger speed of 40 mm/min, with injection of the fluid into open air space through a 16G needle. This however does not mean that fluid injection rate was all the time the same, as it was impossible to know shear rate and respective changes in the fluid viscosity at entering of the needle space and at its rapid expansion leaving the needle. Authors [3] also noted that there was a significant effect of friction between the piston and syringe walls.

Application of these or similar control or measurement methods is not possible in practice, when the medium behaves in a non-conventional way, for instance for shape-memory hydrogels, which collapse upon applied injection pressure and then restoring their shape and volume after leaving the needle [4]. There is no single hydrodynamic flow or material theory able to clearly characterize the injectability of such systems. Only very simplified assumptions (like constant viscosity for laminar Hagen-Poiseueille flow equation) could be employed, but it is well-known they are incapable to describe non-linear behavior of complex fluids.

None of the known existing methods discloses a procedure to measure how big volume of a material would be injected from a specific syringe with a selected needle at proper rate and time, when the needle is inserted at specified depth and angle into a relevant tissue; and which applied force pattern in time would be required for that. Therefore, there is clear need to measure and quantify injectability of a specific fluid from a selected syringe system into realistic tissue objects (and not into free air), as the resistance of tissue to injection might be very different.

After the injection stage has been completed, another problem appears—there is a lack of essential information about the properties, evolution and transient physical maturation of injected biomaterials and tissues where those biomaterials have been injected. The quality of information expected by the user of such methods should be not only sufficiently rigorous to provide scientifically based evidence on the material or tissue, but also to provide acceptable correlations, trends and predictions which can be safely used in design, development and applications of biomaterials. This is especially of concern in cosmetic operations (botox and hyaluronan injections, lipocorrections—fat transfer), as esthetic and medical result often may be far from desired due to formation of bruising, edema, erythema, discoloration, Tyndall effect, relatively short effect time requiring regular injections or surgical procedures, nodules, abnormal tissue migration, excess "hardening" or "softening", etc. [5,6]. Many of such treated tissue properties are rather subjective ("feels OK" vs. "feels not so good") and not quantified; further they are depending on time, patient mood and status and are not easily compared—even for a single person, there are no two fully identical skin or tissue areas which could be tested and validated.

Therefore, it is not enough to only have a method which could quantify the injection process as shown above, but it must be also combined with the method to measure properties of the treated (injected) tissue to compare the results and to make conclusions is this particular formation, injection technique and the material suitable for the purpose before any clinical applications. Furthermore, the framework of the analysis of the injectability and of injected sample should be similar, and preferably model-free. The rationale is that oversimplified fluid models (like a shear-thinning liquid) and tissue models (like a hyper-elastic soft solid) do not provide realistic description of any part of the process nor in the whole, and do not allow correct comparison with the controls. The data quality reported for the same material may also be confusing, as no exact information is given for conditioning changes, and usually no solid proof shown e.g. about suitability of the small strain theory or material linearity [7]. Such conditions are often assumed by default, despite it is of common knowledge that "elastic modulus" or "viscosity" cannot be uniquely defined for material which does not follow linear model.

There is also no single reliable biomechanical test able to get simultaneously a spectrum of invariant functions of the tissue or sample before and after injection, including e.g. sample memory and viscostiffness spectra, characteristic times, intrinsic modulus and viscosity spectra, etc., without assumption of some simplified material model. Here and later, only such tests which do not lead to clear destruction of the specimen, i.e. non-destructive evaluation, are being considered.

SUMMARY OF THE INVENTION

Accordingly, this invention provides solutions that none of the known disclosures are able to provide.

This invention addresses testing of injectability of biomaterials, combined with testing of the object where this biomaterial is injected, for plurality of their properties, especially where these properties are functions depending on testing conditions, in the most cases, in an unknown way.

Furthermore, the invention also addresses obtaining invariant parameters of a plurality of these properties simultaneously with evaluation of the biomaterial injection-treated objects (specimens) without application of pre-selected models of the object material and without assumption of linearity of properties of the object and the injectable material. In addition, the objective of the invention is to use these properties to compare and assess performance of biomaterials and biomaterials-treated specimens where these properties of materials include their testing history. Yet another objective of the invention is to use these obtained invariant properties for prediction of the behavior of the injected material in time.

It is an object of the present invention to provide a method for in vitro testing of injectable materials, especially biomaterials, such as biomaterials for preferential use in medical care like cosmetology, plastic surgery, tissue correction, joints repair, ATMP (advanced therapy medicinal products) or hybrid products with pharmaceutical additions.

The inventor has experimentally discovered that properly controlled prescribed mechanical loading of a injectable biomaterial inside an injection device wherein part of injection device is connected (such as via a needle) with a calibrated tissue object, following by testing of that tissue object with measurement of resulting displacement, displacement rate and strain via same single probe-sensor element can be used to evaluate true time-invariant biomaterial and target object functions within single framework. This framework comprises signals time convolution procedure (including loading history dependence) with idempotent analysis, without use of presumed materials models (such as shear-thinning, thixotropy, elastic, hyperelastic, neo-Hookean, Mooney-Rivlin, etc.) and without need of complex Fourier transform, usually employed in rheology and dynamic mechanical analysis to get real and imaginary parts of the viscoelastic properties.

According to the present invention, an in vitro test method for determining potential capability of a biomaterial to perform in designated clinical conditions is provided. The methods of measurement and data analysis employed in the present invention do not require any prior assumptions about the material, its structure, or behavior. The test method comprises at least the following steps: placing an injectable biomaterial into injection device comprising a plunger and a needle; positioning the injection device onto a sample holder; immersing the needle of the injection device into a target object at a desired depth; establishing a contact of the plunger of the injection device with a sensor probe; applying a mechanical stimulus to the plunger via the sensor probe, said stimulus inducing a movement of the biomaterial from the injection device into the target object; measuring via the same probe changes in a signal reflecting changes in displacement of the plunger as a function of time and applied stimulus; continuing the last two steps until a desired amount of the biomaterial has been injected into the target object; retracting the needle from the target object and repositioning the target object into a second sample holder; positioning the target object onto the second sample holder absent of explicit mechanical fixation of that object; establishing a mechanical contact of the object with a second sensor probe; applying a non-destructive mechanical stimulus to the object via the sensor probe; measuring via the same probe changes in a signal reflecting changes in displacement of the object as a function of time and applied stimulus; subtracting from the signals measured at previous steps contributions from background sources, inclusive the injection device holder, the sensor and measurement device parts themselves; processing measured data by time convolution in a material model-free manner; and calculation of the injectable biomaterial and the target object properties from the processed data.

The injectable biomaterial used in the present invention could be for instance a water-based solution, a hydrogel, or a composite having more than one phase (such as a fluid with solid particles—suspension, or another fluid—emulsion). In some of the embodiments, injectable biomaterial may comprise one or more biological components such as live cells, tissues (like autologous fat) or biological substances, or additions of pharmaceutical preparations, in any relevant combination. In some of the embodiments, the injectable biomaterial is intended to be used for tissue correction, augmentation, cosmetic or plastic surgery purposes.

The target object, where the injection of the biomaterial is being tested, can be a tissue sample, tissue phantom sample, live matter (in vivo; into tissues, organs or tumors, etc.), or any combination thereof, providing that object will be sufficient to be handled into the second phase of the test.

In some of the embodiments, the immersion of the needle of the injection device (syringe) into the target object is made at different inclination angles, relative to the surface of the target object, to mimic a respective clinical practice. Furthermore, such injections can be repeated at different points and at different depths (multiply injections) into the same target object.

The main time-invariant material functions as an example are at least one of the following: biomaterial and target object viscosity, the target object intrinsic modulus, dimensionless memory values, viscostiffnesses. One essential difference of the method of this invention vs. prior art is that mentioned time-invariant properties are calculated from the processed test data by time convolution without application of the Fourier transform, without use of conventional complex numbers algebra, and without an assumption of the material functional properties linearity. This does not exclude that the native signals from the measurement device could be filtered, smoothed or interpolated with Fourier transform but solely with the purpose of noise reduction.

SHORT DESCRIPTION OF THE DRAWINGS

FIGS. 1 A and B present example embodiments of the present invention for the steps of evaluation of the injectabiliity parameters of a biomaterial from a syringe into a right angle (FIG. 1A) or under desired inclination (FIG. 1B).

FIGS. 10 A and B show the predicted change in pressure applied to the syringe in time to ensure the constant injection rate of 0.25 μL/s (FIG. 10A) and the error of prediction vs. set injection rate values (FIG. 10B).

DETAILED DESCRIPTION OF THE INVENTION

Definitions

For the reasons of clarity, the following definitions are used in this invention:

"Advanced Therapy Medicinal Product" (ATMP)—a biomedical product containing or consisting of engineered cells or tissues, and is presented as having properties for, or is used in, or administered to human or animal beings for regenerating, repairing or replacing a human or animal tissue.

"Biomaterial"—a substance (other than a drug or a separate living matter) or combination of substances, which can be used for any period of time, as a whole or as a part of a system which treats, augments, or replaces any tissue, organ, or function of the body of a human or an animal. Some typical examples of injectable biomaterials are water-based solutions, polymers solutions, ceramics suspensions, hydrogels, fluid composites, organic-inorganic hybrids, however it is to be understood that the list is not complete and that novel biomaterials are constantly developed and any and all of such biomaterials are included in the definition of the word in this application.

"Dynamic modulus"—a slope modulus defined as a ratio of dynamic stress amplitude and the dynamic true strain amplitude and expressed in real (not complex) algebra.

"Hybrid product"—a biomedical product having two or more functions in the body (e.g. an implant (biomaterial) with addition of a pharmaceutical substance (drug) or living organisms (ATMP)).

"Idempotent analysis"—a method of mathematical analysis using operations substitution for linearization of a problem to be solved without alteration of initial variables, involving time convolution, observing causality principle (response always comes after the stimulus applied), respecting the boundaries of thermodynamics (no violation of conservation laws), and accounting for non-local effects. It differs from conventional mathematical analysis, where the derivative of a function is always local.

"Injection force"—a value of the force applied to an injection device (like a syringe) to perform the injection of a biomaterial in an object (tissue or tissue phantom)

"Invariant property"—a true (not imaginary or complex) property of a material, which may depend on other properties, but does not depend explicitly on time or frequency of applied stimulus. Time-invariant property also includes specimen loading history data obtained by time convolution [8].

"Materials functions"—properties of a material which are not constants vs. applied mechanical stimuli "Memory value" or "alpha parameter"—a time-invariant property of the specimen, having the value in the range between zero and unity, representing the viscous tendency of the material, even if the material itself is not a fluid. For transport processes like diffusion or wave propagation inside the materials and chemical reactions the alpha value range is between zero and two. In the present description, the term memory values and alpha-values are synonyms.

"Non-destructive evaluation"—a testing method for a material specimen which does not lead to the destruction of the specimen. The specimen tested once could be tested again with the same method even if the specimen has undergone some irreversible changes.

"Object"—a specimen made of tissue phantom, tissue sample, or any similar materials combination wherein the biomaterial injectability is aimed to be tested.

"Slope modulus"—a derivative of the acting stress on the specimen by resulting true strain.

"Stiffness"—a quantity of a specimen to undergo certain deformation under applied prescribed loading.

"Stress"—a ratio of the acting force to the cross-sectional area of the specimen this force is being applied to.

"Time convolution"—a mathematical operation employing integration in time to obtain resulting average values of a property or a function.

"Tissue phantom"—an artificial object or material designed especially to mimic various properties of the natural tissue (example: artificial bone or skin made of different polymers).

"True strain"—a specimen mechanical strain, calculated as natural logarithm of the stretch ratio (instant dimension to initial dimension).

"Viscostiffness"—a time-invariant quantified material function, reflecting link between stiffness and viscosity of the material, determined without assumption of the material model at chosen mode of loading. Together with the simultaneously obtained alpha-value is used to extract other time-invariant parameters such as intrinsic (invariant) moduli, etc.

Thanks to the employed test method according to the present invention, a combined biomaterials characterization is accomplished. The test method of this invention is an in vitro test, referring to a test performed outside a living body. The test method is non-destructive. The test method of this invention comprises at least the following steps:

placing of an injectable biomaterial into injection device comprising a plunger and a needle;
positioning of the injection device onto a sample holder;
immersing the needle of the injection device into a target object at a desired depth;
establishing a contact of the plunger of the injection device with a sensor probe;
applying a mechanical stimulus to the plunger via the sensor probe, said stimulus inducing a movement of the biomaterial from the injection device into the target object;
measuring via the same probe changes in a signal reflecting changes in displacement of the plunger as a function of time and applied stimulus;
continuing the two previous steps until a desired amount of the biomaterial has been injected into the target object;
retracting the needle from the target object and repositioning of the target object into another sample holder;
positioning the target object onto the sample holder absent of explicit mechanical fixation of that object;
establishing a mechanical contact of the object with a sensor probe;
applying a non-destructive mechanical stimulus to the object via the sensor probe;
measuring via the same probe changes in a signal reflecting changes in displacement of the object as a function of time and applied stimulus;
subtracting from the signals measured at injection step and at target object testing step contributions from background sources, inclusive the injection device holder, the sensor and measurement device parts themselves;
processing measured data by time convolution; and
calculating of the injectable biomaterial and the target object properties from the processed data, using at least some of the data for prediction of the target object biomechanical properties at longer times (beyond those observed in experiments).

The injectable biomaterial here refers to a material which purpose is to be injected into a body or tissue in clinical practice. Biomaterials include at least but are not limited to fluids, suspensions, emulsions, hydrogels, polymers, composite and biological materials. The material may also include additional chemical, biological and/or pharmaceutical substances as well as ATMP.

The target object or specimen refers to a piece of a material to be tested after performing test injection of the biomaterial, such as consisting synthetic (tissue phantom), natural or modified materials intended to be, to mimic or to represent a real biological system, or natural tissue specimen where feasible.

Figure 1A:
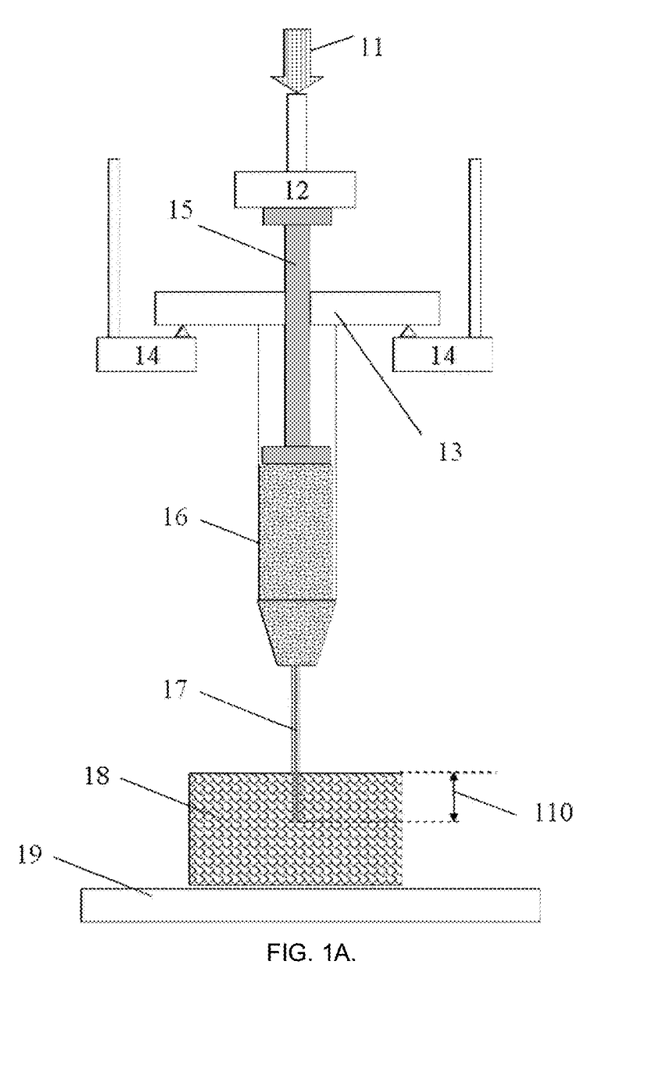
Figure 1B:
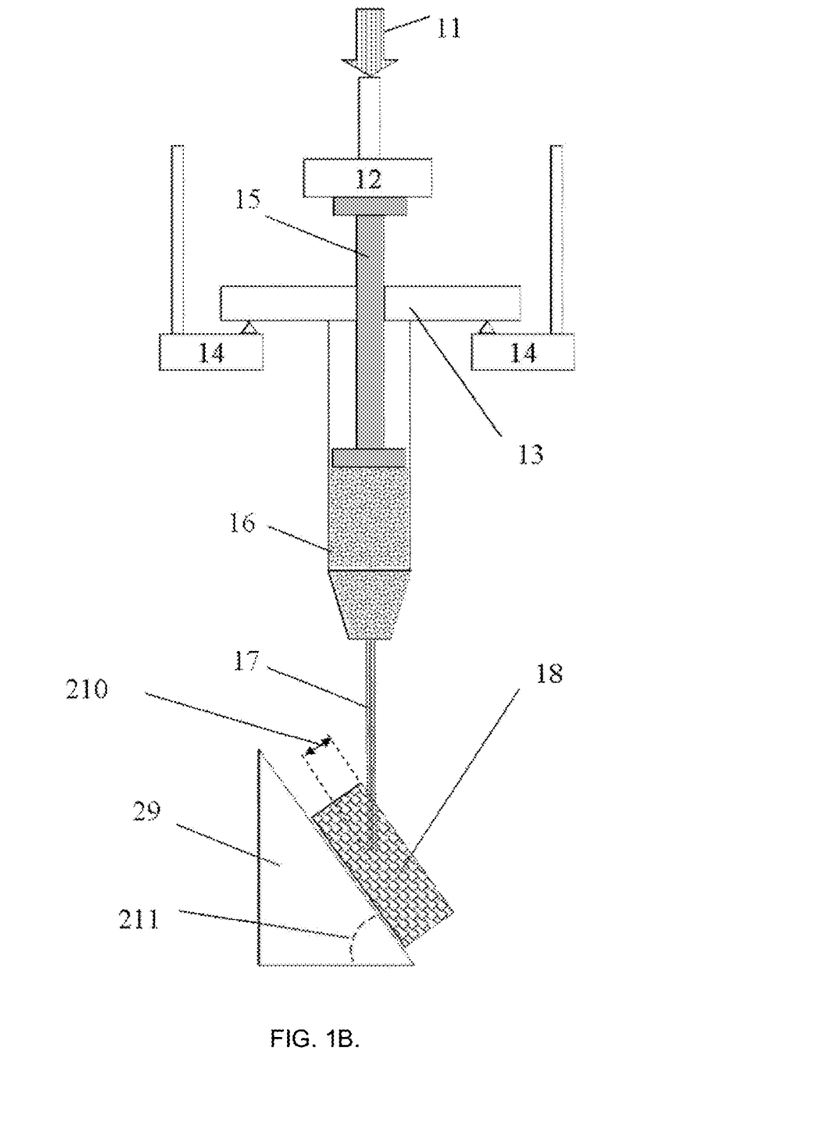

Referring to FIG. 1, in some example embodiments the test method comprises application of non-destructive mechanical force or displacement 11 via probe-sensor 12 to the plunger 15 of the injection device 13. Prior to testing the injection device 13 is positioned on the fixed support 14, and the plunger 15 initial position is recorded after the probe 12 is adjusted to reach a mechanical contact with the plunger 15. During these test steps, injectable biomaterial 16 is pressed to flow through the attached needle 17 with known diameter and length, said this needle is pre-inserted into target object 18 (located on a fixed support 19) on desired depth 110 (FIG. 1A). In another example embodiment (FIG. 1B), the object 18 is alternatively placed on inclined support 29, forming an injection angle 211 in the range between 0 and 90°, where the needle 17 is inserted into object 18 on the depth 210.

Figure 2:
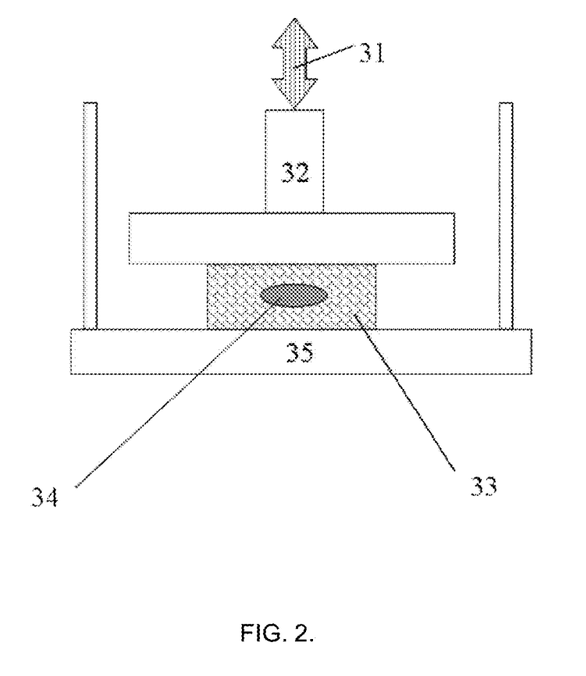
FIG. 2 presents example embodiment of the present invention for the steps of evaluation of the target object with injected biomaterial.

After the injection steps into the target object have been completed, that object is further being tested as for example as depicted in FIG. 2. There the object 33 with injected biomaterial 34 is placed on the fixed support 35 absent of mechanical fixation (gripping or clamping) and subjected to a non-destructive force or displacement stimulus 31, transduced to the object 33 via probe-sensor 32. Absence of mechanical fixation is of a particular importance, as most of practical target object materials cannot be reasonably clamped without affecting their properties.

Figure 3:
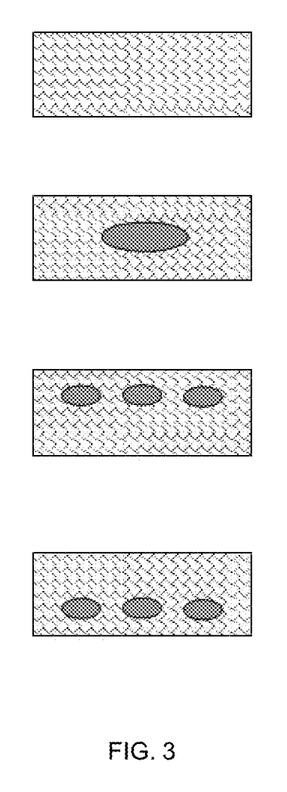
FIG. 3 presents schematic cross-sections of the target objects tested as exhibited in FIG. 2, showing original target object (control without injected biomaterial), object with a single injected biomaterial, and object with multiply injections made as exhibited in FIGS. 1A and 1B, on two different depths.

It is evident for one skilled in the art that such test arrangement could be implemented in different ways. In one example shown in FIG. 3 the amount of injectable biomaterial, its location and depth inside the target object may also vary according to the purpose of the analysis.

The test method is essentially a non-destructive evaluation, wherein the properties of an injectable biomaterial and the target object sample are obtained without causing irreversible mechanical damage to them. This gives a possibility for post-examination the target object on different levels, for example analysis of location and shape of the injected biomaterials by means of e.g. radiography, X-ray scans, ultrasound examination or computer tomography. This allows re-use of the same test specimen for subsequent tests, providing the testing history of the specimen is taken into account.

According to an embodiment, the method provides a combined material characterization, i.e. simultaneous measurement and calculation of plurality of material functions to get an answer whether this material is compatible to the application and whether it is better or worse versus control or reference.

The key element of the data processing is based on time convolution and non-local, causal idempotent analysis [9, 10, 11]. This approach is completely different from commonly used materials laws (models such as elastic, viscoelastic or hyperelastic ones), partial differential equations [12] and complex algebra application (such as commonly used in viscoelastic analysis for estimation of storage and loss moduli). For biological systems one often cannot set up experiments to measure all of the state variables. If only a subset of the state variables can be measured, it is possible that some of the system parameters cannot influence the measured state variables or that they do so in combinations not defining the parameters' effects separately. It is well known that in general case such parameters are unidentifiable and are theoretically inestimable. Thus, a common solution is normally to pre-select a linear model of the system, to guess initial estimates of the values of all parameters and conduct experimental data analysis using that model. The present method does not need such operations. The new method also uses integration with time convolution (global operation) instead of traditional differentiation (local operation), which stabilizes the calculation process and the output.

In brief, the data obtained from the probe-sensor, are digitized, recorded or stored in a form of computer file or as a part of a database using any suitable computer programs, software or subroutines. In some embodiments, such calculations could be performed with pseudo-differentiation [9], direct kernel integration [10], hypergeometric or Wright functions [13]. The present method might be implemented in one or another dedicated computer code or software which specific precision, efficacy and processing time might be chosen depending on the problem addressed and number of the data points to be treated. It is however essential that analysis according to the present invention could be carried out only after the physical test is completed, as time convolution cannot be made until all history data of specimen testing are collected.

The data analysis is taking into account that the knowledge of the full past of a given system does not in general uniquely determine the future development of the system. Hence an observed behavior of the specimen in the future may be a result of different histories (the "butterfly effect": despite an identical behavior in the past, a minimal parameter change may cause a drastic change in the future development of a system). Therefore, after the test history, data have to be accumulated to make non-local idempotent processing meaningful.

The practical effect of time-invariant properties [8] in the method of the invention is that one could see in real application when a biomaterial specimen will be used in a patient.

Yet another essential feature of the above analysis is the comparison of these invariant properties with other specimens or with the control (reference) specimen. This minimizes the risks caused by determination of absolute values at two different time scales. Whereas the comparison can be also carried out for any other measurements, here mapping the time-invariant property A (like viscostiffness) to another property B (like memory value) reveals hidden trends in materials biomechanical behavior, which were discovered by the inventors experimentally (as shown below in the example). These trends might be compared to the reference or target tissue to evaluate how close the test specimen is to this reference or tissue it is supposed to work with.

The main tests parameters (mode, force, displacement, time, frequency, sequence, geometry, fluid, temperature, etc.) can be modified in order to simulate different clinical cases or specific environments. The mechanical stimulus applied to the injectable material comprises mainly compression (not dynamic, as it is impracticable to apply reciprocal pressure to the syringe plunger), but for the target object it comprises of bending, compression, shear or any other similar methods or their combinations, which do not require explicit mechanical fixation of the target object in grips, depending on the material application purpose. The reason for not applying fixation grips is that for many biomaterials and tissues results are strongly depending on the fixation method, clamping force and respective preconditioning thus putting every specimen into different starting position.

The mechanical stimulus has a predetermined intensity, sequence, amplitude, frequency and duration. Also on the contrary to commonly used, this stimulus does not need to be elastic, only being a non-destructive one. According to some embodiments, a mechanical stimulus is applied to injection device, where the needle of this device is inserted into target object on proper depth and inclination, and this applied stimulus causes injectable biomaterial to flow into the target object thus giving direct information of the injectability of the biomaterial without a need to know fluid pressure, strain rate, shear stress or biomaterial viscosity function. Following this, a mechanical stimulus applied in the next steps to the target object comprises providing a predetermined non-destructive force or predetermined deformation with the goal of creation of a true strain and the displacements in the target object specimen close to levels and motions relevant for the intended tissue purpose. Thus, the mechanical stimulus mimics both microstrains and the micromotions of the target object, similar to those occurring when the material is being in a human body.

Advantages of the New Method

The present test method has essential differences from all known injectability testing standards (ISO 7886, ISO 11040), even if one would try to combine them with the target object evaluation steps. The target object evaluation in all known cases relies on traditional classical mechanics and materials models [14, 15]. These differences and advantages are as follows.

First, the method according to the present invention does not stipulate that the target object material has to be compliant with some pre-selected physical model (e.g. elastic, viscoelastic—Kelvin-Voigt, Maxwell, Burgers, Prony series, standard linear solid; hyper elastic, neo-Hookean, Mooney-Rivlin, etc. [15]), and does not need extra assumptions or measurements of e.g. material Poisson ratios, attenuation coefficients, speed of sound, etc.). Selection of the model in any combination is obligatory for any conventional calculations in viscoelastic analysis or in numerical computer simulations like finite element methods, leading to the next step of selection or assumption of the set of biomechanical constants of the material, following these constants evaluation via experimental or modeled fitting of the data to some chosen equations. Whereas the present method can also determine conventional elastic modulus or stiffness of the material specimen, it is not the aim of the invention, as these parameters, usually required by the selected material model, are not generally time invariants and they are not used in the present analysis. New method also overrides needs of explicit use of elastic potentials, strain energy densities, etc. although they also can be additional calculated if specifically required.

Second, the present method does not require the target object having internal homogeneity unless it is the purpose of the material to be homogeneous. On the contrary, tissue phantoms like one used for artificial skin, are highly inhomogeneous and generally cannot be modeled or evaluated unless exact properties of every material layer are known. Variations of specimen local properties are not an obstacle for the testing and data analysis according to the present invention.

Third, the signals of force and displacement are coming out via the same probe sensor acting on the injectable biomaterial and the target object (no separate sensors), and they are not being processed with complex algebra (Fourier transform) for obtaining real ('storage') and imaginary ('loss') parts of the material biomechanical properties. Instead, these signals are being directly recorded during the test and further analyzed by time-convolution and idempotent data processing methods to result into the time-invariant properties, which are the true properties of the material, not linked to any theory or assumption.

Fourth, the experimental viscostiffness obtained with the present method does not require additional tests to be decomposed into true material functions, neither it demands modeling assumptions to make such decomposition.

Fifth, data analysis does not require that applied stimulus signal have some specific waveform (sinusoidal as in dynamic mechanical analysis or rheology) and thus can be applied to any arbitrary one, including non-harmonic oscillations, ramps, stepwise etc., in any sequence.

Sixth, based on the above data analysis there is a possibility to extrapolate results to longer times without assumption of a material model, thus making prediction about expected behavior in future.

Example 1

According to this example, a 1 mL capacity Fortuna® Optima® glass syringe (Poulten & Graf GmbH, Wertheim, Germany) was filled with acrylate polymer-based hydrogel fluid used for disinfection as a model injectable biomaterial of sufficiently high viscosity (GOJO Industries Inc., Akron, Ohio, USA). The syringe was attached with a sterile 26G1/2 size PrecisionGlide® hypodermal needle (Becton Dickinson & Co., Franklin Lakes, N.J., USA) internal needle diameter 0.260 mm) and located at the fixed support according to FIG. 1A in the customized sample holder connected to the dynamic mechanical analyzer DMA242C (Netzsch Gerätebau GmbH, Selb, Germany). The needle was inserted on ~1 mm depth at the right angle into a commercial skin tissue phantom (Simskin LLC, Chicago, Ill., USA), comprising of several layers mimicking epidermis, dermis, hypodermis and fat layers. Tests were carried out at 25±1° C. and normal atmospheric pressure in air.

The test began with moving the probe-sensor of the DMA apparatus until it reached a contact with the glass plunger of the syringe. Than the constant force of 0.5 N was applied to the plunger and the displacement of the plunger was recorded (resolution ±0.0005 µm) within 100-300 sec of the experiment, whereas the same experiment was repeated with other five forces from 0.75 to 2.6 N into different target objects (tissue phantoms). The changed in the displacement in these cases are directly correlated with the volume of the injected substance into the target object, and this requires no knowledge of the fluid pressure inside the syringe, shear stress or shear rate, which clearly are not constants in spatial and time coordinates.

Figure 4:
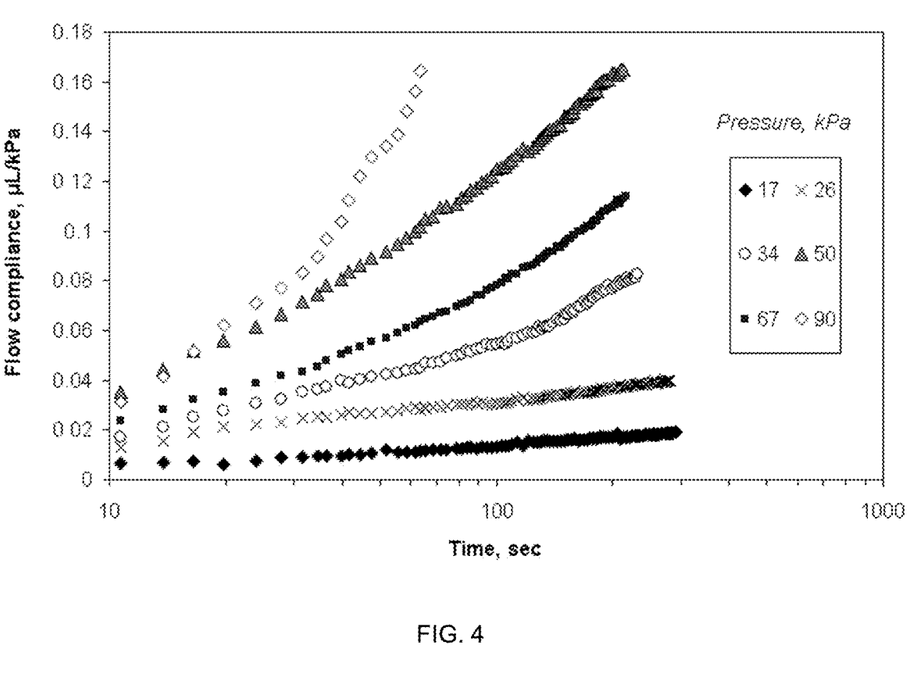
FIG. 4 presents experimental data from the practical example of the embodiment of FIG. 1A, showing the flow compliance (μL/kPa) of injectable material vs. experimental time and applied constant pressure to the syringe plunger.

The amount of the injected material (in µL) was related to the applied constant pressure (in kPa) to result in the flow compliance (µL/kPa), shown in FIG. 4. Here one can see that the flow compliance is not constant with experiment time, being linear only for low pressures. Furthermore, the slope of the compliance curves is not directly proportional to applied pressure being e.g. higher for 50 kPa than for 67 kPa. These features show that the fluid tested is clearly non-Newtonian but it also does not follow any simplified viscosity models (e.g. shear thinning). This is explained due to fact that flow of the material is not only from and through the needle but also into the tissue phantom, which start to oppose incoming fluid volume and at the same time start to undergo its own non-uniform deformation. Thus, data of FIG. 4 include all the effects one may see in a clinical practice during the injection.

To quantify the effect of applied pressure on this process, these data were processed with time-convolution method. For the case of every constant pressure as a parameter (i.e. for every single curve of FIG. 4), the theoretical idempotent solution predicts the power-law formal dependence of compliance vs. time, even if there would be some damped waves propagating through the material [10]:

$$\frac{Q(t)}{P_{appl}} = \frac{t^\alpha}{C_\alpha \Gamma(1+\alpha)} \quad (1)$$

where Q(t) is the volume of the injected material, µL, with time t, $P_{appl}$ is the applied pressure, kPa, $C_\alpha$ is the viscostiffness of the system, kPa·s$^\alpha$, $\Gamma(\cdot)$—gamma-function, α—alpha-parameter (memory value). Resulting numerical values are shown in Table 1.

TABLE 1

Time-invariant values of the injectable material into the tissue phantom.

| Pressure, kPa | Alpha-value | $C_\alpha$, kPa · s$^\alpha$/µL |
|---|---|---|
| 17 | 0.3498 | 415.60 |
| 26 | 0.2696 | 130.35 |
| 34 | 0.4738 | 182.11 |
| 50 | 0.4874 | 88.19 |
| 67 | 0.5057 | 148.44 |
| 90 | 0.9079 | 272.84 |

Figure 5:
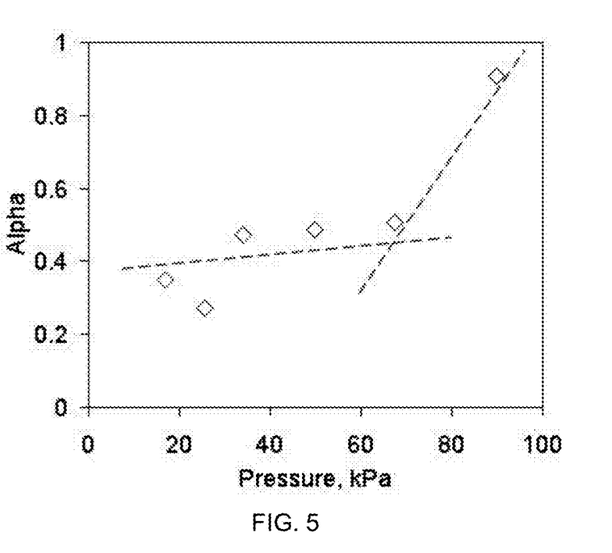
FIG. 5 shows the dependence of the invariant memory value of the injectable material vs. applied pressure, calculated from the data of FIG. 4.

In FIG. 5 the plot of alpha-values vs. pressure is presented, and one may recognize that high pressure above ~70 kPa makes a change in the behavior of the fluid (broken lines are given as a visual guide). When alpha-value ("memory" of the material) is well below 0.5, the system behaves in elasto-viscous manner, and when the value approaches unity, the fluid behavior will dominate. Thus, above 70 kPa one may conclude that the fluid pressure at the injection location becomes a dominating factor, possibly overriding the ability of the target tissue to resist the inflow.

Figure 6:
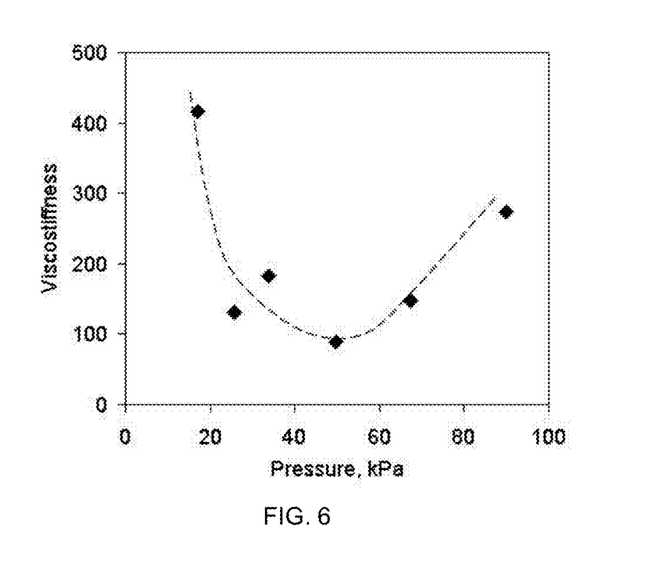
FIG. 6 shows the dependence of the time-invariant viscostiffness (kPa·s$^\alpha$) of the injectable material vs. applied pressure, calculated from the data of FIG. 4 (note a clear non-linearity).

The second important experimental feature is the dependence of the viscostiffness vs. pressure, shown in FIG. 6. One may see that on the contrary to data of FIG. 5 here there is a clear minimum at ~50 kPa. This tells to the user that high viscostiffness values together with low alpha values (seen at low pressures) indicate a "solid material" response to the action. This might be understood as mainly elastic resistance of the tissue phantom to incoming fluid and also as more solid-like fluid movement in the syringe and the needle. However, high viscostiffness at high alpha values (close to unity) tell that the system has changed its response to "fluid material" and starts to approach a very viscous liquid. The minimum of the viscostiffness observed indicates the transition point.

Example 2

The tissue phantom with injected 50±10 μL of the test material as shown in Example 1 was further tested on its biomechanical properties in the manner depicted in FIG. 2. The tissue phantom specimen with external dimensions (l×w×h) (11±0.5)×(12±0.5)×(6.5±0.3) mm was positioned on the sample holder plate and brought into the contact with the probe sensor of 15 mm diameter using compression mode sample holder. The precise size of the tissue phantom specimen was measured with non-contact optical method (±0.5 μm) with laser micrometer (Metralight Inc., CA, USA). The measurements were done before injection and after injection to check that no apparent significant variations (such as specimen twisting or buckling) are present. The other essential details of this measurement and theoretical description are also presented in the non-provisional U.S. patent application Ser. No. 15/655,331 of 20 Jul. 2017.

After letting the probe to establish the contact with the specimen and taring the offset, the dynamic compression test was executed 10 times by stepwise application of dynamic deformation amplitude from 5 to 25 μm at 1 Hz (displacement resolution ±0.0005 μm), corresponding to true strain range 0.001-0.005. For every amplitude value time-point, several oscillation cycles were carried out and thus every data row had to be locally time-convoluted (i.e. within the single set of oscillations at constant amplitudes) values of dynamic and static parameters (forces, displacements, strains, stresses) for every set of cycles. Note that dynamic and static strains are not independent variables, as both involve instant specimen dimensions.

To make a comparison of the resulting properties with the conventional methods, the following material functions were calculated from the experimental data: dynamic modulus (the ratio of stress to true strain), obtained directly from DMA242C control software, and time-invariant alpha-values and viscostiffness, obtained with a present method without use of Fourier transform and complex mathematics. To do this, these measured data were exported as ASCII text file into data processing software (Microsoft Excel complemented with customized code). After that, numerical algorithm of time convolution was applied and processed data were non-locally integrated pair-wisely, row by row. The non-linearity of the applied force and associated change of deformation was taken into account numerically. It might be shown, that in under pure harmonic mechanical excitation with constant frequency f the relation between these values might be in the simplest form written as:

$$|E^*| \approx C_m(\varepsilon) \cdot \omega^{\alpha(\varepsilon)} \qquad (2)$$

where $E^*$ is the complex elastic modulus, kPa, $C_\omega$ is the dynamic viscostiffness, $kPa \cdot s^\alpha$, $\omega$-circular frequency as $2 \cdot \pi \cdot f$, $\alpha$—dynamic memory value, whereas $C_\omega$ and $\alpha$ are in general strain ($\varepsilon$) level dependent.

Figure 7:
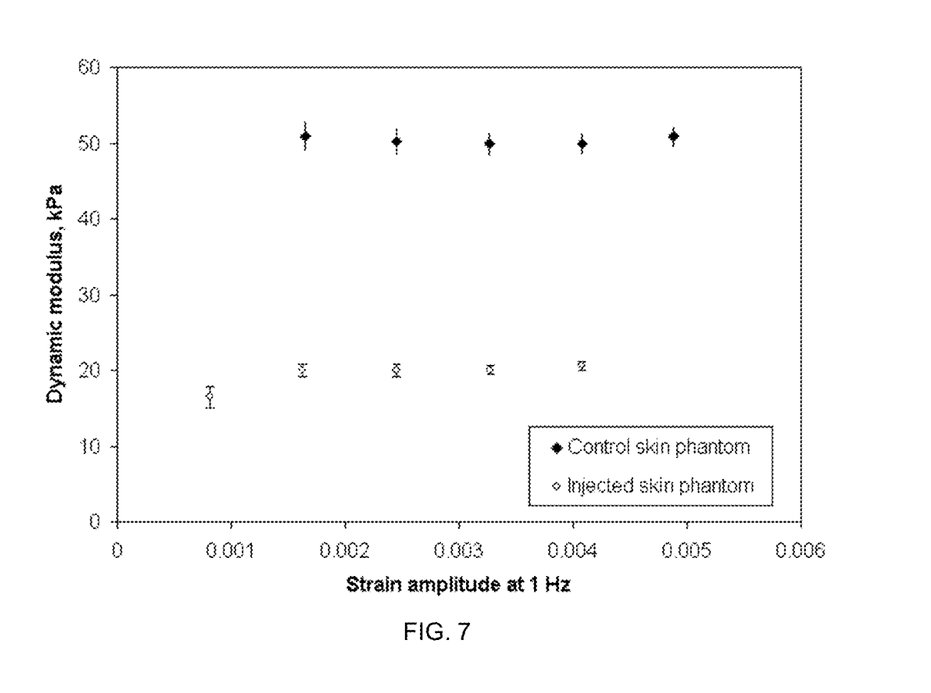
FIG. 7 shows experimental data the practical example of the embodiment of FIG. 2, showing the dynamic modulus of target object (tissue phantom) without and with injected material vs. experimental true strain amplitude at 1 Hz frequency.

Obtained in the conventional way dynamic moduli are shown in FIG. 7 vs. experimental dynamic strain amplitude at 25° C. It is seen that the modulus for control tissue phantom and with one with injected biomaterial are weakly strain-dependent, and that injected specimen has substantially lower modulus value (~20 kPa vs. ~50 kPa at control). With this figure, one might conclude that the tissue phantom properties remain nearly linear but it stiffness decreases by 2.5 times, which might give an indication that the tissue phantom becomes "softer".

Figure 8:
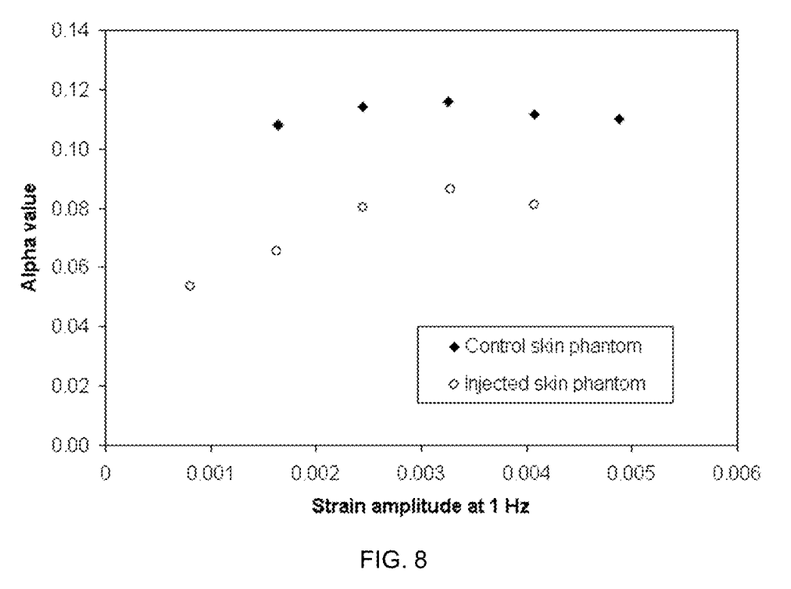
FIG. 8 shows the dependence of the invariant dynamic memory value of the injected and non-injected tissue phantoms vs. experimental true strain amplitude at 1 Hz frequency.

This apparent result however is not correct as the traditional way of calculating modulus via Fourier transform of the spring constant signals in the measuring device cannot result in a time-invariant measure. In FIG. 8 the values of the alpha-parameter (material memory) are plotted vs. strain amplitude which shows that alpha-values for injected tissue phantom are more strain-dependent, whereas for the control phantom they stay nearly constant. Furthermore, these values are lower than for phantom (meaning more solid-like behavior) but increasing with the strain (becoming more fluid-like). This is evidence that the specimen has indeed injected fluid inside, and that fluid has a non-Newtonian behavior.

Figure 9:
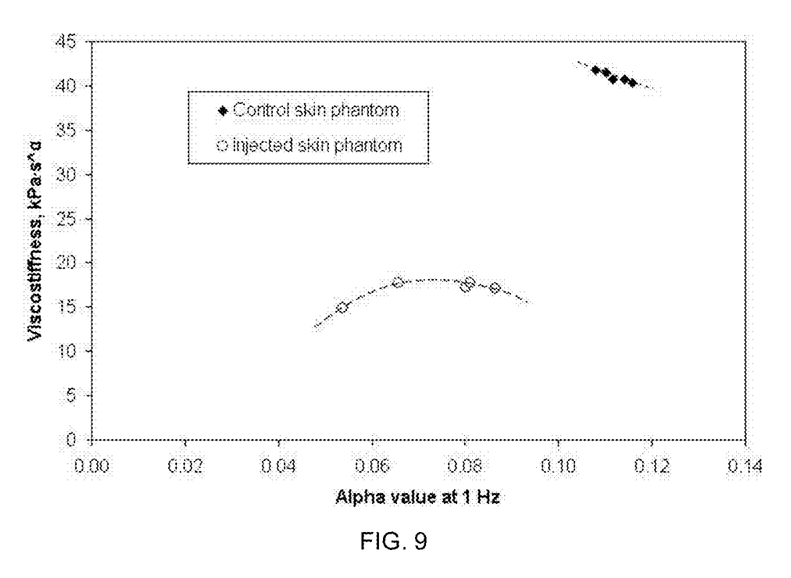
FIG. 9 shows the interrelation of the time-invariant dynamic visco-stiffness and memory values at 1 Hz for the injected and non-injected tissue phantoms.

In FIG. 9, dynamic local time-invariant viscostiffness for the same specimens is plotted vs. respective dynamic memory (alpha-values). In the case the specimen would have been ideally linear material, this plot should have approached a straight line (closer to what is seen for the control specimen). In this example however, it is seen that a non-linearity is present in the injected specimen.

These data result in true intrinsic dynamic modulus of 67.516 kPa for control specimen and of 19.52 kPa for injected specimen, these values being independent not only on time, but also on the strain or stress, so far strains and stresses remain within the limits of the experiment. In addition, the slope of the curves in FIG. 9 allows calculation of tissue phantom material apparent viscosity values from this intrinsic modulus and the exponent factor. For this specimen the effective viscosity is 784 Pa·s for control and 4640 Pa·s for injected specimen respectively.

At the first sight, the values look illogical as "solid" specimen receiving some amount of "liquid" inside become much more "viscous". However, this is the feature the present invention catches clearly as these intrinsic moduli and viscosity values, together with viscostiffness and alpha-parameter describe the whole material and its dynamical behavior which is not possible with conventional approach. In this case, higher apparent viscosity means that injected material undergoes much slower relaxation subjected to the same constant deformation, and for that it will require a smaller amount of mechanical stress (at dynamic loading, but not on static). It might be described as "feeling elastic" but at the same time also "feeling soft touch". Such information is for instance of a great value for development of novel hydrogels for dermal fillers, allowing tailoring them to a proper clinical application and location in the body tissues.

Example 3

In this example, the injectability of the hydrogel material was measured in a similar way to Example 1 but with the purpose to obtain values needed to get constant injection rate. It is anticipated that for maximal patient comfort the injection rate should be kept as constant as possible (minimizing injection pain). This is difficult to achieve with manual syringe or an automated injection gun where injection force (pressure) is set up initially.

The tests were made using DMA242E "Artemis" (Netzsch Gerätebau GmbH, Germany) customized by the applicant. The tests were done at 22±1° C. and RH 25% in a climate-control room under laminar flow cabinet of ISO Class 5 (USP compliant). Plastic syringes (Galderma AB, Sweden) syringes of 1 mL capacity (as used for Restylan® Skin Booster dermal filler) were thoroughly washed several times with deionized water, dried and cleaned from any residual matter and connected with sterile needles 29G×½". Acrylic hydrophilic gel (Gojo Industries Inc. Akron, Ohio, USA) was used as a simulation material—the same as in Example 1. The syringes were filled with ~0.5 mL of the gel and placed into a sample holder (customized by the applicant) of the DMA, FIG. 1. The creep mode of the DMA was chosen with a stepwise force increase on every segment and the protocol was matched to the automatic test execution. There the location of the needle edge was in a polymeric skin phantom (same as used in Example 2) vertically at 90° with the immersion depth of 2 mm to simulate a transdermal injection (FIG. 1).

Figure 10A:
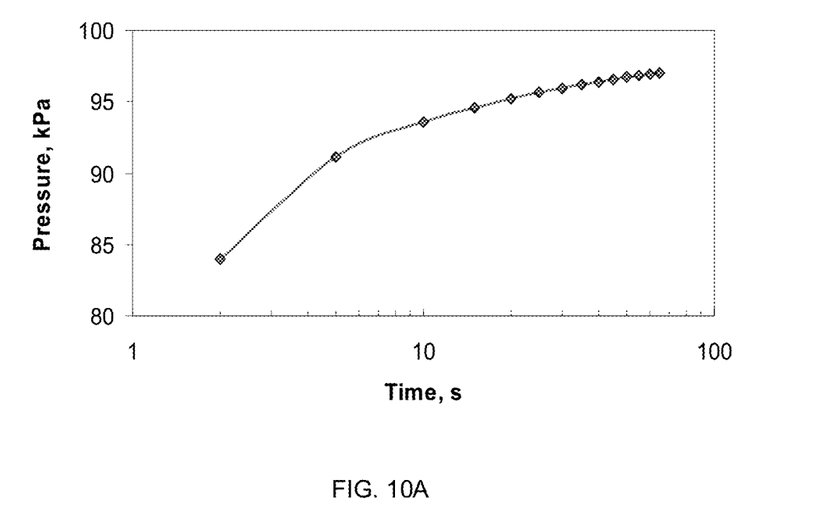
Figure 10B:
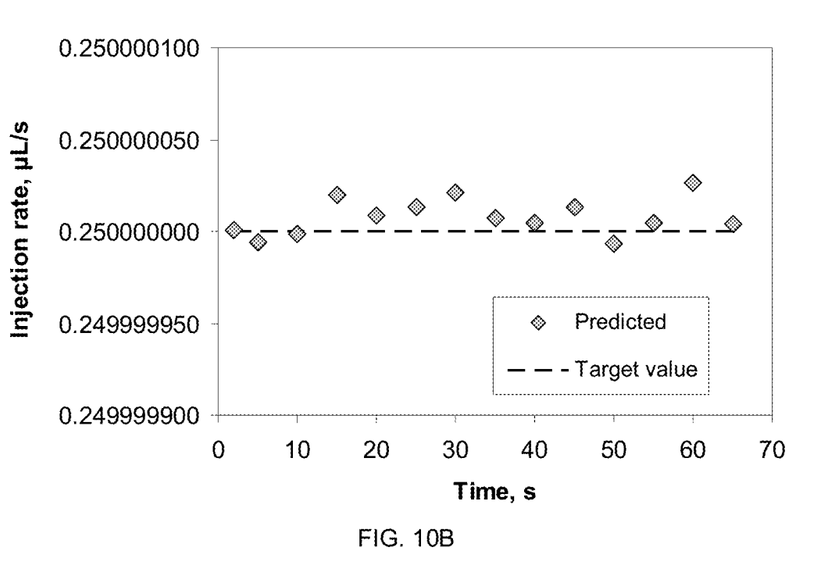

Experimental data were processed in the same way as for Example 1 to obtain invariant parameters according to equation (1) when the respective specific injection rate (μL/s/N) can be expressed after differentiation and rearrangement as $$\frac{\partial F(\tau)}{\partial \tau} = -F(\tau) \cdot \frac{\alpha(F(\tau))-1}{\tau} \quad (3)$$

where F is the unknown force to be applied to the syringe, N at the proper time moment ($\tau$). The challenge in application of Equation (3) is that memory values are force (or pressure) dependent in a non-linear way (FIG. 5). If the fluid is purely Newtonian, than $\alpha=1$ and a force required is constant. For all cases in FIG. 5 the condition $\alpha<1$ holds and the fluid might be considered rheopectic. With dependence of memory values vs. applied pressure or force the flow rate dependence vs. injection time could be solved at some fixed set desired value, and the required pressure could be found to ensure this injection rate at that time moment. In this Example integration of Equation (3) was done using data of FIG. 5 with set desired injection rate of 0.25 μL/s and the required force F for every time step was found by iterative solution of this non-linear equation. These force values are shown in FIG. 10A, and the estimated error of prediction in FIG. 10B. In this particular example one thus starts with 84 kPa pressure increasing it gradually to 96 kPa to provide constant injection rate 0.25 μL/s, giving the relative error well below 0.1 ppm (part per million or <0.00001%). It is noteworthy that injected volume values automatically take into account the previous value of the injected volume (injection history).

Additional Notes

Unlike prior art biomechanical or combined testing methods known to the inventor, the method of the preferred embodiments is internally consistent and directly related to known laws of physics and mathematics rather than dependent on empirical calibrations, a priori assumptions or on pre-selected material models. In use one thus relies on true experimental outcomes rather than artificial fitting of fragments of separate uncoupled values, being often away for clinical conditions.

The above detailed description together with accompanying drawings shows specific embodiments and examples in which the invention can be practiced. Such examples can include elements in addition to those shown or described. However, the inventors also contemplate examples using any combination or permutation of those elements shown or described (or one or more aspects thereof), either with respect to a particular example (or one or more aspects thereof), or with respect to other examples (or one or more aspects thereof) shown or described herein.

The above description is intended to be illustrative, and not restrictive. Also, in the above detailed description, various features may be grouped together to streamline the disclosure, whereas the inventive subject matter may consist less than all features of a particular disclosed embodiment. Although the present invention has been described in more detail in connection with the above examples, it is to be understood that such detail is solely for that purpose and that variations can be made by those skilled in the art without departing from the spirit of the invention except as it may be limited by the following claims. Thus, the following claims are hereby incorporated into the detailed description, with each claim standing on its own as a separate embodiment, and it is contemplated that such embodiments can be combined with each other in various combinations or permutations.

In this document, the terms "a" or "an" are used, as is common in patent documents, to include one or more than one, independent of any other instances or usages of "at least one" or "one or more." Also, in the following claims, the terms "including" and "comprising" are open-ended, that is, a system, device, article, or process that includes elements in addition to those listed after such a term in a claim are still deemed to fall within the scope of that claim. Examples shown in the present invention foresee execution of computer instructions operable to configure and run an electronic measuring device to perform these methods as described. An implementation of such instruction can be realized as a code, such as microcode, assembly language code, a higher-level language code, or user-independent executable code (like a computer program product), whether with or without a graphical user interface, stored or properly located on any computer-readable media during execution or at standby.

REFERENCES

1. Draft Guidance for Industry and FDA staff, Silver Spring, Md., USA, April 2013, 13 p.
2. Aguado B. A., Mulyasasmita W., Su J., Lampe K. J., Heilshorn S. C. Improving viability of stem cells during syringe needle flow through the design of hydrogel cell carriers. Tissue Eng. A18 (2012), 806-815.
3. Silva-Correia J., Gloria A., Oliveira M. B., Mano J. F., Oliveira J. M., Ambrosio L., Reis, R. L. Rheological and mechanical properties of acellular and cell-laden methacrylated gellan gum hydrogels. J. Biomed. Mater. Res. A 101 (2013), 3438-3446.

4. Bencherif S. A., Sands R. W., Bhatta D., Arany P., Verbeke C. S., Edwards D. A., Mooney D. J. Injectable preformed scaffolds with shape-memory properties. PNAS 109 (2012), 19590-19595.
5. Sánchez-Carpintero I., Candelas D., Ruiz-Rodriguez R. Dermal fillers: types, indications, and complications. Actas Dermosifiliogr. 101 (2010), 381-393.
6. Sadick N. S., Karcher C., Palmisano L. Cosmetic dermatology of the aging face. Clinics in Dermatol. 27 (2009), S3-S12.
7. Lujan T. J., Wirtz K. M., Bahney C. S., Madey S. M., Johnstone B., Bottlang M. A novel bioreactor for the dynamic stimulation and mechanical evaluation of multiple tissue-engineered constructs, Tissue Eng. C 17 (2011), 367-374.
8. Xiao H. Invariant characteristic representations for classical and micropolar anisotropic elasticity tensors. J. Elasticity 40 (1995), 239-265.
9. Maslov V. The characteristics of pseudo-differential operators and difference schemes. Actes Congrès intern. Math. 2 (1970), 755-769.
10. Hanyga A., Seredynska M. Power-law attenuation in acoustic and isotropic anelastic media. Geophys. J. Inter. 155 (2003), 830-838.
11. Gunawardena J. An introduction to idempotency. HP Laboratories Bristol, Publication HPL-BRIMS-96-24 (1996), 50 p.
12. Gerisch A., Chaplain M. A. J. Robust numerical methods for taxis-diffusion-reaction systems: applications to biomedical problems. Mathem. Computer Model. 43 (2006), 49-75.
13. Gorenflo R., Luchko Y., Mainardi, F. Analytical properties and applications of the Wright function. Frac. Calc. Appl. Anal. 2 (1999), 383-414.
14. Norris A. Eulerian conjugate stress and strain. J. Mech. Mater. Struct. 3 (2008), 243-260.
15. Maurel W., Wu Y., Thalmann N. M., Thalmann D. Biomechanical models for soft tissue simulation. ESPRIT Publication Series EN18155, Springer (1998), 189 p.

What is claimed is:

1. A method of measurement of properties and performance of injectable biomaterials, said method comprising the steps of:
    a) placing an injectable biomaterial into injection device comprising a plunger and a needle;
    b) positioning the injection device onto a first sample holder;
    c) immersing the needle of the injection device into a target object at a desired depth and inclination;
    d) establishing a contact of the plunger of the injection device with a first sensor probe;
    e) applying a mechanical stimulus to the plunger via the first sensor probe, said stimulus inducing a movement of the biomaterial from the injection device into the target object;
    f) measuring via the first sensor probe a displacement of the plunger and a force applied to the plunger simultaneously as a function of time;
    g) continuing the steps e)-f) until a desired amount of the biomaterial has been injected into the target object;
    h) retracting the needle from the target object and repositioning the target object into a second sample holder;
    i) positioning the target object onto the second sample holder absent of explicit mechanical fixation of that object;
    j) establishing a mechanical contact of the object with a second sensor probe;
    k) applying a non-destructive mechanical stimulus to the object via the second sensor probe;
    l) measuring via the second probe a displacement of the object and a force applied to the object simultaneously as a function of time;
    m) subtracting from the measurements taken at steps f) and l) contributions from background sources, inclusive the injection device holder, the sensor and measurement device parts themselves;
    n) processing measured data obtained in steps f)-g) and l)-m) by time convolution; and
    o) calculating at least one of viscostiffness, alpha value, and flow compliance for the injectable biomaterial and calculating at least one of dynamic modulus, alpha value, and viscostiffness of the target object.

2. The method of claim 1, wherein the method additionally comprises a step for comparing results of the step o) with corresponding results made for a reference injectable material with known properties.

3. The method of claim 1, wherein the method additionally comprises a step for comparing results of step o) with corresponding results for a reference target object with known properties.

4. The method of claim 1, wherein the target object is a tissue sample, tissue phantom sample, live matter, or any combination thereof.

5. The method of claim 1, where the injectable biomaterial is a hydrogel.

6. The method of claim 1, where the injectable biomaterial is a composite having more than one phase.

7. The method of claim 1, where the injectable biomaterial has one or more biological components such as live cells, tissues or biological substances, in any combination.

8. The method of claim 1, where the injectable biomaterial is intended to be used for tissue correction, augmentation, cosmetic or plastic surgery purposes.

9. The method of claim 1, where the injectable biomaterial comprises additions of pharmaceutical preparations.

10. The method of claim 1, wherein the immersion of the needle into the target object is made at different inclination angles relative to the surface of the target object.

11. The method of claim 1, wherein the steps from c) to h) are repeated with the same biomaterials and the same target object at different injection points.

12. The method of claim 1, wherein the calculation of the properties in the step o) is being made model-free for both the injectable biomaterial and for the target object material and used to calculate prediction of the target object biomechanical behavior.

* * * * *